United States Patent
Koyama et al.

(10) Patent No.: US 9,958,330 B2
(45) Date of Patent: May 1, 2018

(54) SENSOR AND INFORMATION ACQUISITION APPARATUS USING SENSOR

(71) Applicant: CANON KABUSHIKI KAISHA, Tokyo (JP)

(72) Inventors: Yasushi Koyama, Kamakura (JP); Toshihiko Ouchi, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 126 days.

(21) Appl. No.: 14/948,108

(22) Filed: Nov. 20, 2015

(65) Prior Publication Data

US 2016/0169746 A1 Jun. 16, 2016

(30) Foreign Application Priority Data

Nov. 28, 2014 (JP) .................................. 2014-242519

(51) Int. Cl.
*G01J 5/08* (2006.01)
*G01N 21/3581* (2014.01)

(52) U.S. Cl.
CPC ........... *G01J 5/0825* (2013.01); *G01J 5/0837* (2013.01); *G01N 21/3581* (2013.01)

(58) Field of Classification Search
CPC .................................................. G01J 5/0825
See application file for complete search history.

(56) References Cited

U.S. PATENT DOCUMENTS

| 4,339,660 A * | 7/1982 | Buchholz ................ G01S 7/499 250/221 |
| 7,689,070 B2 | 3/2010 | Ouchi |
| 9,234,797 B1 * | 1/2016 | Newman .................. G01J 3/28 |
| 2003/0178584 A1* | 9/2003 | Arnone ............. G01N 21/3581 250/495.1 |
| 2005/0231421 A1* | 10/2005 | Fleisher ................. G01S 7/411 342/179 |
| 2006/0085160 A1* | 4/2006 | Ouchi ................ G01N 21/3581 702/150 |
| 2013/0001421 A1* | 1/2013 | Pyo .......................... G01J 3/42 250/330 |

(Continued)

FOREIGN PATENT DOCUMENTS

JP 2004-177198 A 6/2004
JP 2006-145513 A 6/2006

*Primary Examiner* — David Porta
*Assistant Examiner* — Jeremy S Valentiner
(74) *Attorney, Agent, or Firm* — Canon U.S.A., Inc. IP Division (57) ABSTRACT

A sensor to detect information on a subject by using an electromagnetic wave includes a transmitting unit having a generating element and a first antenna, a polarization converting unit, and a receiving unit having a second antenna and a detecting device. The generating element generates an electromagnetic wave, and the first antenna emits the electromagnetic wave generated by the generating element as first polarization. The polarization converting unit converts the first polarization into second polarization by changing a polarization direction of the first polarization. The second antenna receives the second polarization, and the detecting device detects the electromagnetic wave received by the second antenna. The transmitting unit and the receiving unit are disposed on the same substrate.

20 Claims, 5 Drawing Sheets

(56) References Cited

U.S. PATENT DOCUMENTS

2013/0307716 A1* 11/2013 Mohamadi ............ G01S 13/887
                                                     342/22
2014/0326890 A1* 11/2014 Debray .................... G01J 5/10
                                                    250/349
2015/0256733 A1*  9/2015 Kanamori ............ H04N 5/2354
                                                    348/234

* cited by examiner

SENSOR AND INFORMATION ACQUISITION APPARATUS USING SENSOR

BACKGROUND OF THE INVENTION

Field of the Invention

The present invention relates to a sensor that generates and detects a terahertz wave, and an information acquisition apparatus using the sensor.

Description of the Related Art

Research and development have been recently performed on application of a terahertz wave (in this specification, an electromagnetic wave of frequency of from 30 GHz to 30 THz) to industrial fields, such as communication, security, and medical. A terahertz wave has penetration capability and rectilinearity, and can acquire inside information of an object with high resolution by reflection signals and transmission signals from the object. Therefore, various nondestructive and noninvasive inspection techniques are developed.

Ultrashort pulse laser or a high intensity magnetic field, an ultralow temperature environment, and the like have been required for generation and detection of the terahertz wave. Therefore, a measuring apparatus for sensing and imaging is large in size and complicated in configuration. As a means to reduce size and weight of such a measuring apparatus, Japanese Patent Laid-Open No. 2006-145513 discloses a generating element that generates a terahertz wave, and an imaging system using a semiconductor diode for a detecting device that detects the terahertz wave. The detecting device detects the terahertz wave penetrated through or reflected on a subject, and acquires a penetration image or a reflection image of the subject. U.S. Pat. No. 7,689,070 discloses a small-sized sensor in which a transmitting unit and a receiving unit of a terahertz wave, and an antenna that combines the terahertz wave and space are integrated and modularized. The sensor improves portability of a measuring apparatus.

The terahertz wave emitted from the transmitting unit may be reflected on an optical member disposed in an optical path between the transmitting unit of the sensor and the receiving unit of the sensor, and may be multiply reflected between the optical member, the subject, and the like. When such a reflective terahertz wave enters a transmitting unit of a small-sized sensor in which semiconductor devices with high coherence property, such as a semiconductor diode, output of the transmitting unit may be destabilized. That is, the reflected terahertz wave may enter the transmitting unit of the sensor and characteristics of the generating element may change, whereby output of the transmitting unit of the sensor may be destabilized.

SUMMARY OF THE INVENTION

According to an aspect of the present invention, a sensor to detect information on a subject by using an electromagnetic wave includes a transmitting unit having a generating element configured to generate an electromagnetic wave, and a first antenna configured to emit the electromagnetic wave generated by the generating element as first polarization, a polarization converting unit configured to convert the first polarization into second polarization by changing a polarization direction of the first polarization and a receiving unit having a second antenna configured to receive the second polarization, and a detecting device configured to detect the electromagnetic wave received by the second antenna, wherein the transmitting unit and the receiving unit are disposed on the same substrate.

Further features of the present invention will become apparent from the following description of exemplary embodiments with reference to the attached drawings.

DESCRIPTION OF THE EMBODIMENTS

Embodiment

Figure 1A:
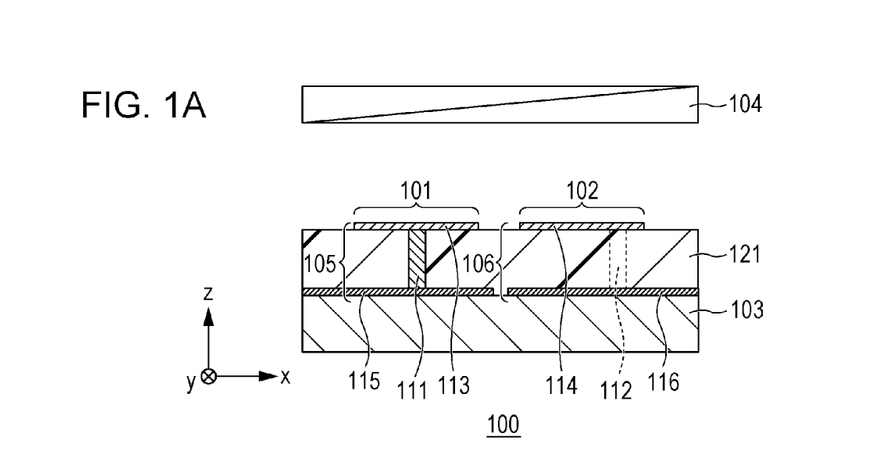
FIG. 1A is a cross-sectional view of a configuration of a sensor according to an embodiment and Example 1.
Figure 1B:
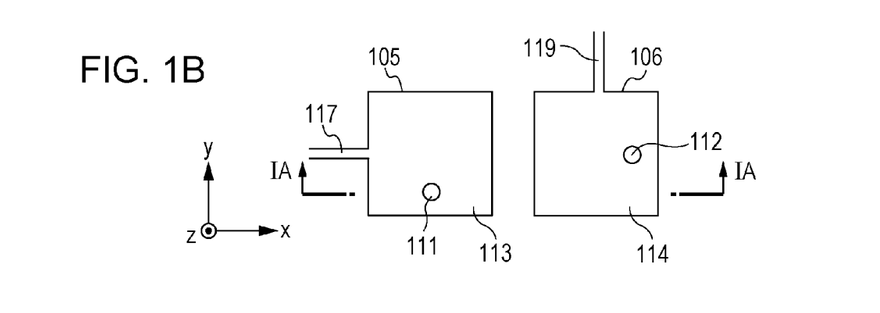
FIG. 1B is a top view of a configuration of a sensor according to an embodiment and Example 1.
Figure 1C:
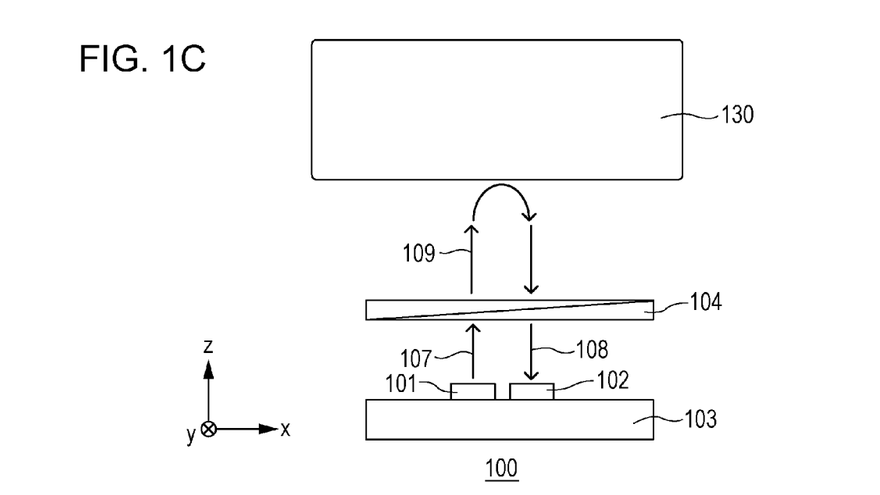
FIG. 1C schematically illustrates generation and detection of a terahertz wave using a sensor according to an embodiment and Example 1.

Generation and detection of a terahertz wave using a sensor 100 according to the present embodiment is described with reference to FIG. 1C. FIG. 1C schematically illustrates generation and detection of a terahertz wave using the sensor 100. A frequency of a terahertz wave is equal to or higher than 30 GHz and equal to or lower than 30 THz.

The sensor 100 is a small-sized, high-resolution sensor that generates and detects a terahertz wave, thereby detecting information on a subject using an electromagnetic wave. The sensor 100 is provided with a substrate 103, a transmitting unit 101 and a receiving unit 102 integrated on the substrate 103, and a polarization converting unit 104. The transmitting unit 101 generates first polarization 107. In the present embodiment, the first polarization 107 is a terahertz wave of a frequency $f_{THz}$, and is linear polarization. The polarization direction of the first polarization 107 emitted from a first antenna 105 of the transmitting unit 101) is changed by the polarization converting unit 104. Then, the first polarization 107 is converted into a terahertz wave (i.e., third polarization) 109 including a circular polarization component or an elliptic polarization component, and is applied to a subject 130.

The "polarization direction" herein refers to an oscillation direction of an electric field of a terahertz wave. Further, "to change the polarization direction" herein includes changing linear polarization into elliptic polarization or circular polarization, and changing only an angle of linear polarization. Linear polarization is polarization of which polarization plane is limited to one plane. Elliptic polarization is polarization of which electric field (or magnetic field) vector rotates with time. Circular polarization is polarization of which locus becomes a circle when an electric field vector end is projected on a plane perpendicular to a forward direction of a terahertz wave.

The polarization direction of the third polarization 109 reflected on the subject 130 is again changed by the polarization converting unit 104, and is converted into a terahertz wave (i.e., second polarization) 108 which is linear polarization. The polarization direction of the second polarization 108 crosses the polarization direction of the first polarization 107. It is desirable that the polarization direction of the second polarization 108 and the polarization direction of the first polarization 107 cross perpendicularly. Hereinafter, the polarization direction of the first polarization 107 is referred to as a first polarization direction, and the polarization direction of the second polarization 108 is referred to as a second polarization direction.

The first antenna 105 of the transmitting unit 101 is selectively combined with a terahertz wave of the first polarization direction (the first polarization 107), but is not combined with a terahertz wave of the second polarization direction (the second polarization 108) that crosses the first polarization direction. A second antenna 106 of the receiving unit 102 is combined with the second polarization 108 of the second polarization direction converted by the polarization converting unit 104, and selectively receives the second polarization 108. With this configuration, entering, into the transmitting unit 101, of the terahertz wave which is reflected on an optical member (not illustrated) disposed on an optical path of the terahertz wave between the transmitting unit 101 and the receiving unit 102, the subject 130, and the like may be reduced. Therefore, a change in the characteristic of a generating element 111 of the transmitting unit 101 and, therefore, destabilization of output of the generating element 111 that generates the terahertz wave may be reduced.

Further, it may be reduced that a part of the terahertz wave reflected on the optical member (not illustrated) disposed on the optical path of the terahertz wave between the transmitting unit 101 and the receiving unit 102, the subject 130, and the like interferes with the second polarization 108 to detect, and is detected by the receiving unit 102. Therefore, a fluctuation in intensity and the like of detection signals of the receiving unit 102 are reduced.

In the present embodiment, the first polarization 107 and the second polarization 108 are linear polarizations, and the first polarization direction and the second polarization direction cross each other. However, the present invention is not limited to this configuration: it is only necessary that the polarization state of the first polarization 107 and the polarization state of the second polarization 108 differ from each other. In that case, it is only necessary that the first antenna 105 is selectively combined with the terahertz wave of the polarization state of the first polarization 107, and the second antenna 106 is selectively combined with the terahertz wave of the polarization state of the second polarization 108.

Here, "the first antenna 105 is selectively combined with the first polarization 107" refers to that, if the first antenna 105 is irradiated with the first polarization 107 and polarization of which polarization state differs from that of the first polarization 107, the first antenna 105 is combined more efficiently with the first polarization 107. Similarly, "the second antenna 106 is selectively combined with the second polarization 108" refers to that the second antenna 106 is combined more efficiently with the second polarization 108 than polarization of which polarization state differs from that of the second polarization 108. This means that the first antenna 105 is configured to be combined more efficiently with the first polarization 107 than with the second polarization 108, and that the second antenna 106 is configured to be combined more efficiently with the second polarization 108 than with the first polarization 107.

A configuration of the sensor 100 is described. FIG. 1A is a cross-sectional view and FIG. 1B is a top view of a configuration of the sensor 100. The sensor 100 is provided with the transmitting unit 101, the receiving unit 102, the substrate 103, and the polarization converting unit 104 as described above. The transmitting unit 101 and the receiving unit 102 are disposed side by side on the same substrate (i.e., the substrate 103). The transmitting unit 101 and the receiving unit 102 may be current injection devices that generate or detect an electromagnetic wave under electrical control, which may suitably reduce the size of the sensor 100.

The sensor 100 may have a pair of or a plurality of pairs of the transmitting unit 101 and the receiving unit 102 disposed on the same substrate. The height of a surface, from the bottom surface of the substrate 103, on which the transmitting unit 101 is located and the height of a surface, from the bottom surface of the substrate 103, on which the receiving unit 102 is located may be the same or different. The distance between the transmitting unit 101 and the receiving unit 102 and the distance between adjoining receiving units 102 are desirably as short as possible, and desirably are set to be equal to or shorter than twice the wavelength of the terahertz waves (the first polarization 107, the second polarization 108 and the third polarization 109) used for generation and detection. With this configuration in which the subject 130 is irradiated with the terahertz wave and the reflected terahertz wave is received by the receiving unit 102, the terahertz wave can be detected with higher resolution.

If the sensor 100 is provided with a plurality of transmitting units 101 and a plurality of receiving units 102, these transmitting units 101 and the receiving unit 102 may be arranged in any form. For example, one transmitting unit 101 and one receiving unit 102 may be arranged alternately and corresponding to each other. Alternatively, one transmitting unit 101 and a plurality of receiving units 102 may be arranged corresponding to one another, or a plurality of transmitting units 101 and one receiving unit 102 may be arranged corresponding to one another. Alternatively, a plurality of transmitting units 101 and a plurality of receiving units 102, which are different in frequency of the generated terahertz wave and frequency of detectable terahertz wave, may be integrated to thereby configure a sensor that can sense in a wide frequency range.

The material of the substrate 103 may be selected depending on application of the sensor 100. The substrate 103 may be made of, for example, semiconductors, such as silicon, gallium arsenide, indium arsenide, and gallium phosphorus, or resins, such as glass, ceramics, Teflon (registered trademark), and polyethylene terephthalate.

The transmitting unit 101 oscillates the first polarization 107 which is linear polarization in the first polarization direction. The transmitting unit 101 is provided with a semiconductor layer as a generating element 111 that generates a terahertz wave of frequency $f_{THz}$, and the first antenna 105 combined with the terahertz wave in the first polarization direction. The generating element 111 may be made of a negative resistance device (i.e., a differential negative resistance device) that has a gain in a terahertz wave region. Alternatively, the generating element 111 may be made of, for example, quantum cascade laser (QCL) which is an active layer generating a terahertz wave by transition of a career between subbands. The generating element 111 of the present embodiment is a negative resistance device, and is an element in which a region where a current decreases with an increase in voltage in current-voltage characteristics, i.e., a region with negative resistance, appears.

As the negative resistance device, typically, high frequency elements, such as a resonant tunneling diode (RTD), an Esaki diode, a Gunn diode, and a transistor terminated at one terminal thereof are preferably used. Further, a TUNNETT diode, an IMPATT diode, a heterojunction bipolar transistor (HBT), a compound semiconductor FET, a high-electron mobility transistor (HEMT), and so on may be used. Negative resistance of a Josephson device using a superconductor may also be used. Hereinafter, a case where RTD which is a typical negative resistance device operating at a terahertz band is used for the generating element 111 is described.

The first antenna 105 is combined with the terahertz wave in the first polarization direction and functions as a resonator and a radiator. The first antenna 105 may be an antenna having polarization dependency, such as a microstrip antenna, a slot antenna, a half wavelength dipole antenna, a loop antenna, and a folded-dipole antenna. In the present embodiment, a case where a patch antenna which is a resonator in a terahertz wave band and a kind of microstrip resonators using a microstrip line of limited length and the like, is used as the first antenna 105 is described.

The first antenna 105 is provided with a first patch conductor 113, a first ground conductor 115, and a dielectric layer 121. The dielectric layer 121 is disposed between the first patch conductor 113 and the first ground conductor 115. Here, the "dielectric material" refers to a material of which dielectricity is dominant to electrical conductivity, and which behaves as an insulating material or a high resistor that does not conduct electricity with respect to a DC voltage. Typically, the dielectric material is preferably a material having resistivity of 1 kΩ·m or greater. Specifically, resins, plastics, ceramics, silicon oxide, silicon nitride, and the like may be used.

The generating element 111 is disposed between the first patch conductor 113 and the first ground conductor 115. Since the generating element 111 is electrically connected with each of the first patch conductor 113 and the first ground conductor 115, the first antenna 105 and the negative resistance device are electrically connected with each other. Therefore, the transmitting unit 101 has an active antenna in which the first antenna 105 and the generating element 111 are integrated, and the width of the first patch conductor 113 in the y axial direction is set to $\lambda/2$ resonator length with respect to the terahertz wave of frequency $f_{THz}$.

The transmitting unit 101 oscillates a terahertz wave of resonance frequency $f_{THz}$ of a parallel resonant circuit combined with the first antenna 105 and the reactance of a negative resistance device as the generating element 111. The generating element 111 is disposed at a position shifted in the y axial direction from the centroid of the first patch conductor 113 and, thereby, the first antenna 105 emits first polarization of which polarization direction is the y axial direction upward (i.e., in the +z axial direction) perpendicular to the substrate 103.

A bias circuit for adjusting a bias voltage supplied to the negative resistance device as the generating element 111 is provided with an unillustrated power supply and wiring 117. The power supply (not illustrated) supplies a current necessary for driving the generating element 111, and adjusts the bias voltage. The bias voltage is selected typically from the negative resistance region of the generating element 111. The bias voltage is supplied to the negative resistance device of the generating element 111 from the wiring 117.

The wiring 117 is desirably disposed at a position that becomes a node of the electric field of the terahertz wave of frequency $f_{THz}$ standing in the first antenna 105. The wiring 117 has high impedance at frequency bands near frequency $f_{THz}$. Here, the "position that becomes a node of the electric field of the terahertz wave of frequency $f_{THz}$ standing in the first antenna 105" refers to a position at which field intensity of the terahertz wave of frequency $f_{THz}$ standing in the first antenna 105 decreases by one figure. Typically, a position at which field intensity of the terahertz wave of frequency $f_{THz}$ standing in the antenna 105 is equal to or smaller than $1/e^2$ of the maximum field intensity (e is a base of the natural logarithm) is desirable. Shunt resistance and parallel capacity for reducing parasitic oscillation of low frequency wave may be disposed between the first antenna 105 and the power supply (not illustrated).

The receiving unit 102 receives and detects a terahertz wave (second polarization) of which polarization direction is the second polarization direction. In the sensor 100, the second polarization direction crosses the first polarization direction. The receiving unit 102 is provided with the second antenna 106 that receives the second polarization, and a detecting device 112 that detects a terahertz wave received by the second antenna 106.

The detecting device 112 detects the terahertz wave received by the second antenna 106, and converts the detected terahertz wave into an electrical signal. Various materials may be used as the detecting device 112. For example, a rectifier is known as an element that can implement an element operating at frequency of 1 THz or higher. Especially, a Schottky barrier diode (SBD) is suitable for the detecting device 112 because it functions at a terahertz wave band and operates at a room temperature. The rectifier may be a semiconductor of which nonlinearity of the career is located at the frequency domain of the terahertz wave. For example, a region in which nonlinearity of the current is produced due to a voltage change in current-voltage characteristics of RTD may also be used.

A thermal type detecting device and a quantum type detecting device may also be used as the detecting device 112 of the terahertz wave. Examples of the thermal type detecting devices may include a microbolometer (e.g., a-Si and VOx), a pyroelectric device (e.g., LiTaO3 and TGS), and a golay cell. These thermal type detecting devices convert a change in physical properties caused by electromagnetic wave energy into heat, convert a temperature change due to heat into, for example, thermoelectromotive force or resistance, and detect an electromagnetic wave.

Examples of the quantum type detecting devices may include an intrinsic semiconductor element (e.g., an MCT (HgCdTe) photoconductive element) or an impurity semiconductor element. These quantum type detecting devices capture the electromagnetic wave as a photon and detect photoelectromotive force or a resistance change of a semiconductor of a small band gap. Hereinafter, in the present embodiment, a case where SBD, which is a representative detecting device operating at a terahertz wave band, is used for the detecting device 112 is described.

In SBD as the detecting device 112, ohmic metal, a high carrier concentration semiconductor, a low carrier concentration semiconductor, and Schottky metal are stacked in this order from the substrate side. A second patch conductor 114 and a second ground conductor 116 are electrically connected to Schottky metal (unillustrated) and ohmic metal (unillustrated), respectively, thereby enabling extraction of a rectified current of SBD and voltage control. By adjusting the position of the detecting device 112 in the x axial direction and the structure of SBD, which is the detecting device 112, impedance matching between the impedance of the second antenna 106 and the impedance of the detecting device 112 is adjusted.

The second antenna 106 may be, similar to the first antenna 105, an antenna having polarization dependency, such as a microstrip antenna, a slot antenna, a half wavelength dipole antenna, a loop antenna, a folded-dipole antenna, and the like. In the present embodiment, an example in which a patch antenna is used as the second antenna 106 is described.

The second antenna 106 is provided with the second patch conductor 114, the second ground conductor 116, and the dielectric layer 121. The dielectric layer 121 is disposed between the second patch conductor 114 and the second ground conductor 116. That is, the dielectric layer 121 is sandwiched between the two conductors, the second patch conductor 114, and the second ground conductor 116. In the second antenna 106, the width of the second patch conductor 114 in the x axial direction is set to $\lambda/2$ resonator with respect to the terahertz wave of frequency $f_{THz}$.

The detecting device 112 is disposed between the second patch conductor 114 and the second ground conductor 116, and is combined with the second antenna 106 by being electrically connected with each of the second patch conductor 114 and the second ground conductor 116. The detecting device 112 is disposed at a position shifted in the x axial direction from the center of the second patch conductor 114, whereby the second polarization in the resonant direction of the second antenna 106 can be selectively received. That is, the second antenna 106 is combined with polarization with high efficiency in the second polarization direction that crosses the first polarization direction combined with the first antenna 105.

The detecting device 112 detects the second polarization 108 by rectifying the terahertz wave, received by the second antenna 106, of frequency $f_{THz}$ as the second polarization 108 of which polarization direction is the x axial direction, and converting the rectified terahertz wave into an electrical signal. The electrical signal from the receiving unit 102 is transmitted via electrical wiring 119, and is processed by an integrated electronic circuit (not illustrated). The second polarization 108 of the present embodiment enters the substrate 103 from above in the direction perpendicular to the surface of the substrate 103 in the −x axial direction with respect to the second antenna 106.

The polarization converting unit 104 functions as a first converting unit that changes the polarization direction of the first polarization 107, and a second converting unit that changes the polarization direction of the third polarization 109. That is, the first converting unit and the second converting unit are integrated in the present embodiment. A quarter wavelength plate (quarter wave plate, Quarter-wave retarder) is used in the present embodiment.

The polarization converting unit 104 is disposed between the transmitting unit 101 and the subject 130 and between the receiving unit 102 and the subject 130. That is, the polarization converting unit 104 is disposed on a propagation path between transmission of the terahertz wave from the transmitting unit 101 and arrival at the subject 130, and on a propagation path between reflection of the terahertz wave on the subject 130 and entering in the receiving unit 102.

A crystal axis of the quarter wavelength plate as the polarization converting unit 104 (hereafter, referred to as a "quarter wavelength plate 104") is set in the direction to rotate with respect to an optical axis of the first polarization 107 and the second polarization 108 (i.e., in the z axial direction). The crystal axis of the quarter wavelength plate 104 is set in the direction in which the first polarization 107 emitted from the transmitting unit 101 is reflected on the subject 130, and enters the receiving unit 102 as the second polarization 108 which crosses the polarization direction of the first polarization 107.

A well-known material of the quarter wavelength plate 104 is X-cut quartz. $LiNbO_x$, $LiTaO_x$, $NbTaO_x$, KTP, DAST, ZnTe, GaSe, GaP, CdTe, and the like which are nonlinear optical crystals may also be used. Alternatively, AR coating, such as polyethylene or valylene, may be applied to a surface of the quarter wavelength plate 104 to reduce reflection of the first polarization 107 and the third polarization 109 entering the quarter wavelength plate 104.

The first polarization 107 emitted from the first antenna 105 is converted into the terahertz wave (the third polarization) 109 including a circular polarization component or an elliptic polarization component by the quarter wavelength plate 104 as the first converting unit. After being emitted from the quarter wavelength plate 104, the third polarization 109 is applied to the subject 130. The third polarization 109 reflected on the subject 130 enters the quarter wavelength plate 104 as the second converting unit integrated with the first converting unit, and is converted into the second polarization 108. Since the second antenna 106 is configured to combine with the terahertz wave of the polarization state of the second polarization 108, the second antenna 106 receives the second polarization 108, which is rectified by the detecting device 112 and is converted into an electrical signal.

The second antenna 106 functions also as a polarization filter that selectively receives the second polarization 108 converted by the quarter wavelength plate 104. That is, since entering of the terahertz wave other than the second polarization 108 into the detecting device 112 can be reduced, an influence of the interference of the terahertz wave reflected outside is reduced, and a fluctuation in intensity of the detection signal in the detecting device 112 can be reduced.

The first antenna 105 of the transmitting unit 101 functions also as a polarization filter that is combined selectively with the terahertz wave of the polarization state in the first polarization 107, and not combined with the second polarization direction that crosses the first polarization direction. With this configuration, entering, into the receiving unit 102, of the second polarization 108 reflected on the subject 130 or an external member and returned can be reduced. Therefore, in the sensor 100, destabilization of output of the transmitting unit due to the interference of the terahertz wave reflected outside is reduced.

Desirably, the first polarization and the second polarization are set to be linear polarizations, and the electric field direction of the first polarization is set to be the direction of 45° with respect to a fast axis or a slow axis of the quarter wavelength plate 104, whereby effects that are more significant can be produced. Here, the quarter wavelength plate 104 is crystal having birefringence. Since a refractive index of the quarter wavelength plate 104 differs depending on the crystal orientation, the propagation rate differs depending on the oscillation direction of the entered linear polarization. In the description above, the fast axis has a small refractive index and corresponds to a crystal orientation of an oscillation direction in which entered linear polarization travels faster, and the slow axis has a large refractive index and corresponds to a crystal orientation of an oscillation direction in which entered linear polarization travels slow.

Since a phase difference of 90° is produced in the fast axis direction and the slow axis direction in the quarter wavelength plate 104 in the first polarization 107, the terahertz wave (i.e., the third polarization) 109 emitted from the quarter wavelength plate 104 becomes circular polarization. The third polarization 109 reflected on the subject 130 is converted by the quarter wavelength plate 104 into linear polarization with a phase difference of 90°, and the second polarization 108 after passing through the quarter wavelength plate 104 becomes linear polarization rotated 90° with respect to the polarization direction of the first polarization. The polarization direction of the terahertz wave transmitted when combined with the first antenna 105 and the polarization direction of the terahertz wave received by the second antenna 106 cross at right angles, whereby the first antenna 105 and the second antenna 106 operate as polarization filters more effectively.

With this configuration, as described above, entering, into the transmitting unit 101, of the terahertz wave reflected on an optical member (not illustrated) disposed on an optical path of the terahertz wave between the transmitting unit 101 and the receiving unit 102, the subject 130, and the like may be reduced. That is, an influence of the terahertz wave reflected on the optical member (not illustrated) disposed on the optical path of the terahertz wave between the transmitting unit 101 and the receiving unit 102, the subject 130, and the like may be reduced. Therefore, destabilization of output of the generating element 111 that generates the terahertz wave may be reduced.

Further, a fluctuation in intensity of the detection signal of the receiving unit 102 due to an interference of the terahertz wave reflected on an optical member (not illustrated) disposed on an optical path of the terahertz wave between the transmitting unit 101 and the receiving unit 102, the subject 130, and the like may be reduced.

Example 1

The configuration of the sensor 100 of the embodiment described above is described in more detail. The sensor 100 transmits and receives a terahertz wave of frequency $f_{THz}$=0.45 THz.

The generating element 111 of the transmitting unit 101 is RTD. The RTD used in Example 1 has, for example, a multiple quantum well structure by InGaAs/InAlAs and InGaAs/AlAs on the substrate 103 and an electrical contact layer by n-InGaAs. An InP substrate is used for the substrate 103 in Example 1. An exemplary multiple quantum well structure is a triple barrier structure. Specifically, the substrate 103 is formed by a semiconductor multilayer structure of AlAs (1.3 nm)/InGaAs (7.6 nm)/InAlAs (2.6 nm)/InGaAs (5.6 nm)/AlAs (1.3 nm). Among these, InGaAs is a well layer and lattice matching InAlAs and non-matching AlAs are barrier layers. These layers are left undoped, for which intentional career doping is not performed.

Such a multiple quantum well structure is sandwiched between electrical contact layers of n-InGaAs of which electron concentration is $2\times10^{18}$ cm$^{-3}$. In a current voltage I(V) characteristic of the structure between the electrical contact layers, the peak current density is 280 kA/cm2, and a region about 0.7V or more and about 0.9V or less is a differential negative resistance region. If the RTD as the generating element 111 has a mesa structure of about 2 μmΦ, the peak current becomes 10 mA and the differential negative resistance becomes −20Ω.

The first antenna 105 is provided with the RTD of the generating element 111, and a square-shaped patch antenna with the first patch conductor 113 which is about 200 μm each side. Benzocyclobutene (BCB, manufactured by The Dow Chemical Company, $\in_r$=2.4) which is about 3 μm in thickness is disposed as the dielectric layer 121 between the first patch conductor 113 and the first ground conductor 115.

The 2-μm-diameter RTD as the generating element 111 is disposed between the first patch conductor 113 and the first ground conductor 115, and is electrically connected with the patch conductor 113 and the ground conductor 115. The generating element 111 is disposed at a position shifted by 80 μm from the centroid of the first patch conductor 113 in the y axial direction which is a resonant direction. The first antenna 105 is combined with a terahertz wave of which polarization direction is the y axial direction, and the transmitting unit 101 emits, in the +z axial direction, a terahertz wave of which polarization direction is the y axial direction and of which frequency $f_{THz}$ is 0.45 THz.

The receiving unit 102 is provided with the second antenna 106 and the detecting device 112. The detecting device 112 includes SBD. The SBD as the detecting device 112 used in Example 1 has a structure in which metal film is formed on a semiconductor layer including epitaxially grown n-InP (~$10^{17}$ cm$^{-3}$)/n+InP on the substrate 103. The height of the semiconductor layer is about 100 nm. Specifically, about 30-nm-thick nickel film, which is a Schottky electrode, is formed on the n-InP side, and Ti/Pd/Au film, which is an ohmic electrode, is formed on the n+InP side, whereby the detecting device 112 has about 2-μm mesa structure.

In the second antenna 106, the dielectric layer 121 is sandwiched between the square-shaped patch conductor 114 which is about 200 μm each side and the second ground conductor 116. The second antenna 106, having the detecting device 112 disposed between the second patch conductor 114 and the second ground conductor 116, operates as a patch antenna. Benzocyclobutene (BCB, manufactured by The Dow Chemical Company, $\in_r$=2.4) which is about 3 μm in thickness is used for the dielectric material 121.

The detecting device 112 including the SBD formed in the 2-μm mesa structure is disposed between the second patch conductor 114 and the second ground conductor 116, and is electrically connected with the second patch conductor 114 and the second ground conductor 116. The detecting device 112 is disposed at a position shifted by 80 μm from the centroid of the second patch conductor 114 in the x axial direction, which is the resonant direction, in consideration of impedance matching with the second antenna 106. The receiving unit 102 receives the terahertz wave of which polarization direction is the x axial direction and of frequency $f_{THz}$=0.45 THz entering from +z axial direction. That is, the semiconductor layer as the generating element 111 as the generating element is disposed at a position shifted from the centroid of the first patch conductor 113, and the detecting device 112 is disposed at a position shifted from the centroid of the second patch conductor 114. Here, a line connecting the generating element 111 and the centroid of the first patch conductor 113 and a line connecting the detecting device 112 and the centroid of the second patch conductor 114 cross each other. In the sensor 100, the polarization direction of the polarization combined with the second antenna 106 of the receiving unit 102 and the polarization direction of the polarization combined with the first antenna 105 of the transmitting unit 101 cross each other.

The quarter wavelength plate 104 becomes a quarter wavelength plate with respect to a terahertz wave of which frequency $f_{THz}$ is 0.45 THz. In the quarter wavelength plate

104, AR coating consisting of 1-µm-thick valylene is formed on a 100-µm-thick x cut quartz. The quarter wavelength plate 104 is installed at a position separated by 3 mm from the surface of the substrate 103.

The sensor 100 of Example 1 is fabricated in the following manner. First, the following layers are made to epitaxially grow on the substrate 103 by, for example, molecular beam epitaxy (MBE) or organic metal vapor phase epitaxy (MOVPE). Specifically, n+InGaAs, an InGaAs/InAlAs layer which becomes RTD, n+InGaAs, and an n-InP/n+InP layer which becomes SBD are made to epitaxially grow in this order on the substrate 103.

After the n−InP/n+InP layer in the region including RTD of the generating element 111 is removed, the generating element 111 is etched in a 2 µm-diameter arc mesa shape. Subsequently, a 2-µm-square mesa structure is etched in the region including SBD of the detecting device 112. Etching may be electron beam (EB) lithography and dry etching by (inductively coupled plasma (ICP). Photolithography may also be used.

The first ground conductors 115 and the second ground conductors 116 are formed on the etched surface by liftoff. The first ground conductors 115 and the second ground conductors 116 are embedded with BCB as the dielectric layer 121 by spin coating and dry etching. A first patch conductor 113 of Ti/Pd/Au is formed on the mesa structure of the generating element 111 including RTD by liftoff, a second patch conductor 114 of nickel/Au is formed on the mesa structure of detecting device 112 including SBD. Finally, the wirings 117 and 119, a power supply (not illustrated), an integrated circuit (not illustrated), and so on are connected by, for example, wire bonding, and an x cut quartz plate is mounted precisely on the substrate 103 by machinery mounting, whereby the sensor 100 is completed.

In Example 1, a triple barrier RTD consisting of InGaAs/InAlAs and InGaAs/AlAs grown up on an InP substrate has been described as RTD which is the generating element 111. However, these structures and materials are illustrative only and not restrictive. For example, an RTD with a double barrier quantum well structure, and an RTD with a four-fold or more multiple barrier quantum well may be used. The SBD as the detecting device 112 may be, similarly, configured by a semiconductor, such as GaAs, InP, and Si. These structures and materials may be selected suitably depending on desired frequency and the like.

The following combination may be used for the material.
GaAs/AlGaAs/formed on GaAs substrate and GaAs/AlAs, InGaAs/GaAs/AlAs
InGaAs/AlGaAsSb formed on InP substrate
InAs/AlAsSb and InAs/AlSb formed on InAs substrate
SiGe/SiGe formed on Si substrate An operation of the sensor 100 of Example 1 is described. The terahertz wave (the first polarization) 107 of the first polarization emitted from the first antenna 105 of the transmitting unit 101 is converted into the terahertz wave (the third polarization) 109 of the circular polarization by the quarter wavelength plate 104. The third polarization 109 of the circular polarization reflected on the subject 130 is converted into the terahertz wave (the second polarization) 108 of the second polarization which crosses perpendicularly the first polarization within the quarter wavelength plate 104. The first antenna 105 of the transmitting unit 101 is selectively combined with the first polarization 107, but is not combined with the second polarization 108 of which polarization direction crosses that of the first polarization 107 at right angles. The second antenna 106 of the receiving unit 102 receives the second polarization selectively.

According to the sensor 100 of Example 1, entering, into the transmitting unit 101, of the terahertz wave reflected on an optical member (not illustrated) disposed on an optical path of the terahertz wave between the transmitting unit 101 and the receiving unit 102, the subject 130, and the like may be reduced. Therefore, destabilization of output of the generating element 111 that generates the terahertz wave may be reduced.

Further, a fluctuation in intensity of the detection signal of the receiving unit 102 due to an interference of the terahertz wave reflected on an optical member (not illustrated) disposed on an optical path of the terahertz wave between the transmitting unit 101 and the receiving unit 102, the subject 130, and the like may be reduced. Therefore, a small sized, high resolution sensor capable of obtaining a terahertz wave stably is implementable.

A modification of the sensor 100 of Example 1 is described hereinafter. The same configurations as those of the sensor 100 are denoted by the same reference numerals, and detailed description thereof is omitted.

Figure 2A:
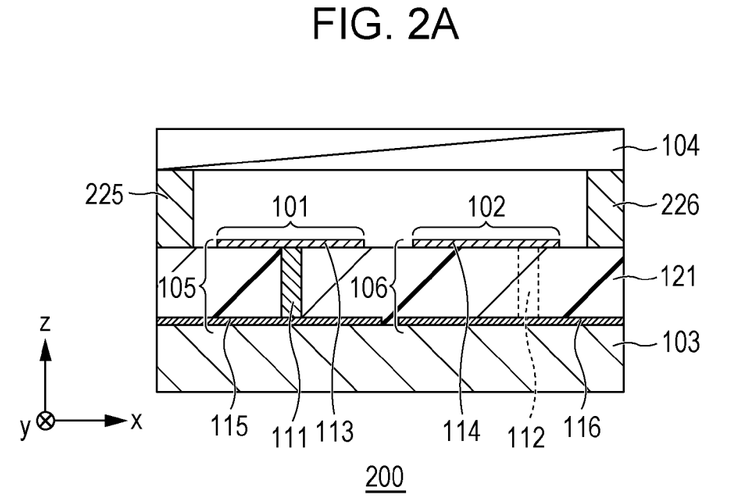
FIG. 2A schematically illustrates a sensor according to a first modification of Example 1.

FIG. 2A schematically illustrates a configuration of a sensor 200, which is a first modification of the sensor 100. In the sensor 200, a quarter wavelength plate 104 as a polarization converting unit is mounted on a substrate 103 together with a transmitting unit 101 and a receiving unit 102. Specifically, the quarter wavelength plate 104 is disposed, using spacers 225 and 226, on a propagation path of a terahertz wave transmitted from the transmitting unit 101 and on a propagation path of a terahertz wave entering the receiving unit 102. With this configuration, an unnecessary interference may further be reduced by adjusting a distance between the quarter wavelength plate 104 and the transmitting unit 101 and between the quarter wavelength plate 104 and the receiving unit 102. Further, a possibility the transmitting unit 101 and the receiving unit 102 of the sensor 200 become dirty due to contact with the subject 130 and the like is reduced.

Figure 2B:
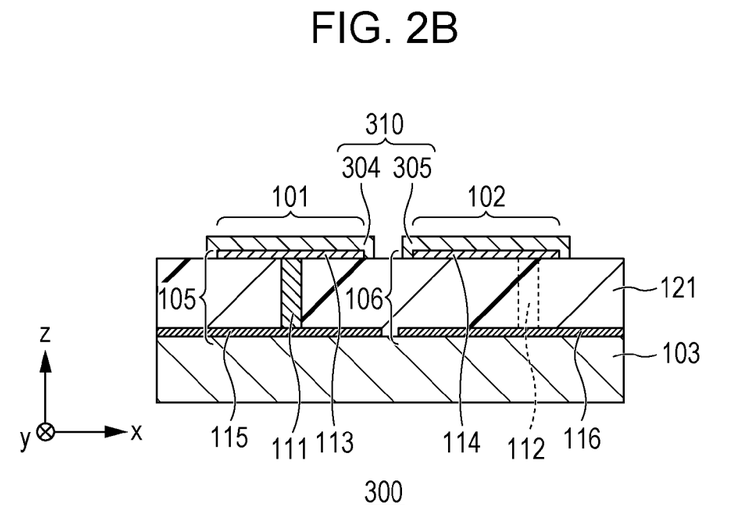
FIG. 2B schematically illustrates a configuration of a sensor according to a second modification of Example 1.

FIG. 2B schematically illustrates a configuration of a sensor 300, which is a second modification of the sensor 100. The sensor 300 is provided with a polarization converting unit 310 that includes a first converting unit 304 and a second converting unit 305. Each of the first converting unit 304 and the second converting unit 305 is a quarter wavelength plate. The first converting unit 304 is disposed on a propagation path on which first polarization 107 emitted from the transmitting unit 101 propagates before arriving at a subject. The second converting unit 305 is disposed on a propagation path on which the third polarization 109 reflected on the subject propagates before entering the receiving unit 102. In Example 1, the first converting unit 304 is disposed on the first patch conductor 113, and the second converting unit 305 is disposed on the second patch conductor 114.

Further, as described above, entering, into the transmitting unit 101, of the terahertz wave reflected on an optical member (not illustrated), the subject 130, and the like disposed on an optical path of the terahertz wave between the transmitting unit 101 and the receiving unit 102 may be reduced. Therefore, destabilization of output of the generating element 111 that generates the terahertz wave may be reduced. Further, a fluctuation in intensity of the detection signal of the receiving unit 102 due to an interference of the terahertz wave reflected on an optical member (not illustrated) disposed on an optical path of the terahertz wave between the transmitting unit 101 and the receiving unit 102, the subject 130, and the like may be reduced. Therefore, a small sized, high resolution sensor capable of obtaining a terahertz wave stably is implementable. According to the configuration of this modification, the sensor 300 can be smaller than the sensor 100.

Figure 3:
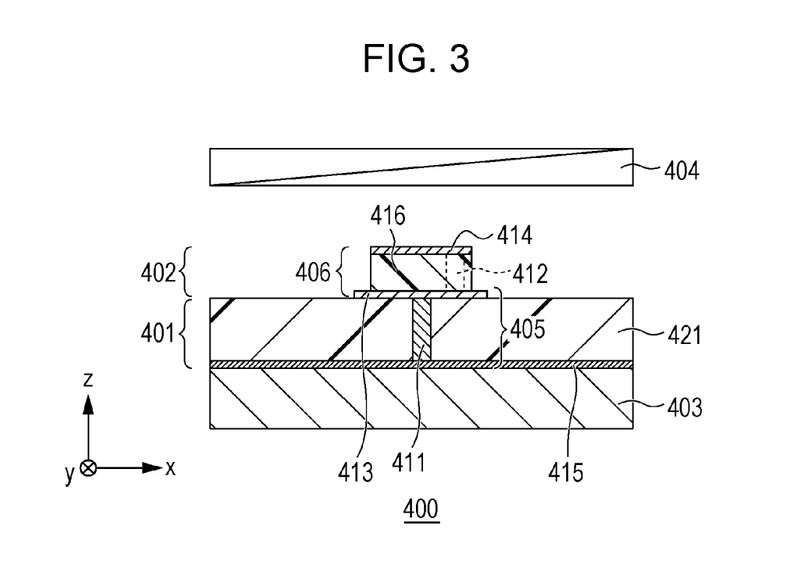
FIG. 3 schematically illustrates a configuration of a sensor according to a third modification of Example 1.

FIG. 3 schematically illustrates a configuration of a sensor 400, which is a third modification of the sensor 100. The sensor 400 is provided with a transmitting unit 401 and a receiving unit 402 stacked in this order on a substrate 403. Further, a quarter wavelength plate 404 as a polarization converting unit is disposed on a propagation path of a terahertz wave transmitted from the transmitting unit 401 and on a propagation path of a terahertz wave that enters the receiving unit 402. The transmitting unit 401 includes the first antenna 405 and the generating element 411. The receiving unit 402 includes the second antenna 406 and the detecting device 412.

A first antenna 405 is provided with a conductor 413, a ground conductor 415, and a first dielectric layer 421 disposed between the conductor 413 and the ground conductor 415. A second antenna 406 is provided with a patch conductor 414, a conductor 413, and a second dielectric layer 416 disposed between the patch conductor 414 and the conductor 413. The conductor 413 functions as a patch conductor of the antenna 405 and as a ground conductor of the second antenna 406.

Also in a configuration in which the receiving unit 402 is disposed (i.e., stacked) on the transmitting unit 401, the sensor 400 has the quarter wavelength plate 404 and polarization selectivity of the first antenna 405 and the second antenna 406. Therefore, entering, into the transmitting unit 401, of the terahertz wave reflected on an optical member (not illustrated) disposed on an optical path of the terahertz wave between the transmitting unit 401 and the receiving unit 402, the subject 130, and the like may be reduced. Therefore, destabilization of output of the generating element 411 that generates the terahertz wave may be reduced. Further, a fluctuation in intensity of the detection signal of the receiving unit 402 due to an interference of the terahertz wave reflected on an optical member (not illustrated) disposed on an optical path of the terahertz wave between the transmitting unit 401 and the receiving unit 402, the subject, and the like may be reduced. Therefore, a small sized, high resolution sensor capable of obtaining a terahertz wave stably is implementable. This configuration is suitable for a high resolution small sized sensor.

Figure 4:
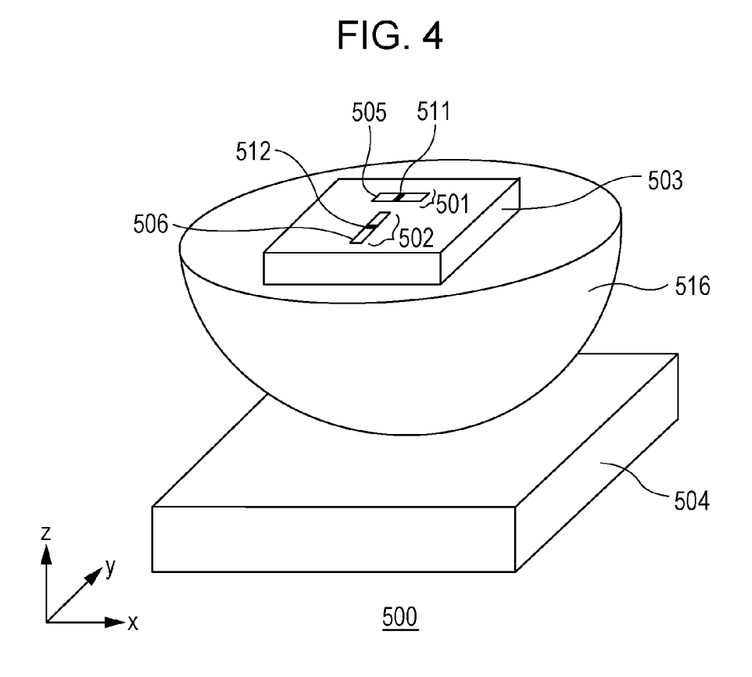
FIG. 4 schematically illustrates a configuration of a sensor according to a fourth modification of Example 1.

FIG. 4 schematically illustrates a configuration of a sensor 500 which is a fourth modification of the sensor 100. The sensor 500 includes the transmitting unit 501 and the receiving unit 502. The transmitting unit 501 includes the first antenna 505 and the generating element 511. The receiving unit 502 includes the second antenna 506 and the detecting device 512. The sensor 500 uses slot antennae as a first antenna 505 of a transmitting unit 501 and as a second antenna 506 of a receiving unit 502.

That is, the sensor 500 includes a conductor as the substrate 503 and the first antenna 505 and the second antenna 506 are slot antennae including openings provided in the substrate 503. In this case, the longitudinal direction of the opening as the first antenna 505 and the longitudinal direction of the opening as the second antenna 506 cross each other. Therefore, the first antenna 505 is combined more efficiently with first polarization 107 than with second polarization 108, and the second antenna 506 is combined more efficiently with the second polarization 108 than with the first polarization 107. The sensor 500 is provided with a lens 516 and a quarter wavelength plate 504 as a polarization converting unit. The transmitting unit 501 and the receiving unit 502 are the same as the transmitting units and the receiving units that of above-described embodiments except for the configurations of the first antenna 505 and the second antenna 506. Lens 516 is a silicone lens.

The lens 516 and the quarter wavelength plate 504 are disposed on a propagation path of a terahertz wave transmitted from the transmitting unit 501 and on a propagation path of a terahertz wave entering the receiving unit 502. The first antenna 505 emits, toward the substrate 503, a terahertz wave which polarizes in the y axial direction. The terahertz wave enters the quarter wavelength plate 504 via a lens 516. The terahertz wave is applied to an unillustrated subject, reflected on the subject, is converted into a terahertz wave polarized in the x axial direction by the quarter wavelength plate 504, and received and detected by the second antenna 506 via the lens 516 and the substrate 503.

The sensor 100 employs a patch antennae as the first antenna 105 and the second antenna 106, but other antennae may be used. For example, an antenna having polarization dependency, such as a microstrip antenna, a slot antenna, a half wavelength dipole antenna, a loop antenna, and a folded-dipole antenna may be used.

According to the sensors of the first to the fourth modifications, entering, into the transmitting unit, of the terahertz wave reflected on an optical member (not illustrated) disposed on an optical path of the terahertz wave between the transmitting unit and the receiving unit, the subject, and the like may be reduced. That is, an influence of the terahertz wave reflected on the optical member (not illustrated) disposed on the optical path of the terahertz wave between the transmitting unit 101 and the receiving unit 102, the subject 130, and the like may be reduced.

Therefore, destabilization of output of the generating element 511 that generates the terahertz wave may be reduced. Further, a fluctuation in intensity of the detection signal of the receiving unit due to an interference of the terahertz wave reflected on an optical member (not illustrated) disposed on an optical path of the terahertz wave between the transmitting unit and the receiving unit, the subject, and the like may be reduced. Therefore, a small sized, high resolution sensor capable of obtaining a terahertz wave stably is implementable.

Example 2

Figure 7:
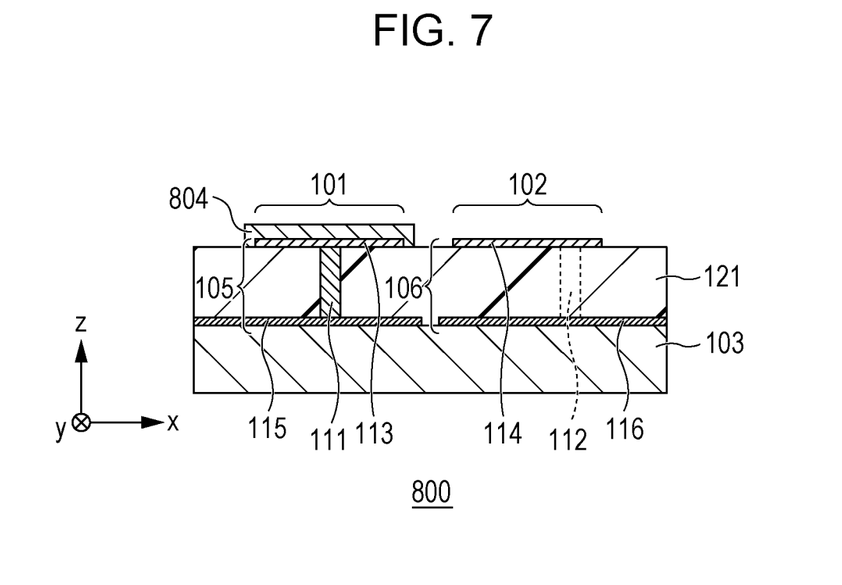
FIG. 7 schematically illustrates a configuration of a sensor of Example 2.

A sensor 800 of Example 2 is described. FIG. 7 schematically illustrates a configuration of the sensor 800. A polarization converting unit 310 of sensor 300 of Example 1 is provided with the first converting unit 304 that changes the polarization direction of the first polarization 107 combined with the first antenna 105 of the transmitting unit 101, and the second converting unit 305 that changes the polarization direction of the terahertz wave and converts into the second polarization 108 combined with the second antenna 106 of the receiving unit 102. That is, the first polarization 107 is converted into the second polarization 108 using the first converting unit 304 and the second converting unit 305. In contrast, the sensor 800 of Example 2 receives, by a receiving unit 102, a terahertz wave obtained by changing the polarization direction of the first polarization 107 transmitted from the transmitting unit 101. The same configurations as those of the sensor 300 are denoted by the same reference numerals and, detailed description thereof is omitted.

The sensor 800 is provided with a polarization converting unit 804 that changes the polarization direction of a first polarization 107 and converts into a second polarization 108. The polarization converting unit 804 is disposed above the first patch conductor 113 so that the polarization direction of the terahertz wave transmitted from the transmitting unit 101 can be changed. In Example 2, a quarter wavelength plate is used as the polarization converting unit 804.

In this case, for example, the first antenna 105 is combined with circular polarization, and the second antenna 106 is combined with linear polarization in an arbitrary direction. With this configuration, the transmitting unit 101 transmits circular polarization as the first polarization 107. The first polarization 107 is converted into linear polarization (i.e., second polarization) 108 in an arbitrary direction by the polarization converting unit 804, and is applied to a subject. The second polarization 108 reflected on the subject is combined with the second antenna 106 and is therefore detected by a detecting device 112 of the receiving unit 102.

The polarization converting unit 804 is provided on the transmitting unit 101 side in Example 2, but it may be provided on the receiving unit 102 side. The first antenna 105 is combined with circular polarization and the second antenna 106 is combined with the linear polarization, but an inverted configuration may be employed.

According to the sensor 800 of Example 2, entering, into the transmitting unit 101, of the terahertz wave reflected on an optical member (not illustrated) disposed on an optical path of the terahertz wave between the transmitting unit 101 and the receiving unit 102, the subject, and the like may be reduced.

That is, an influence of the terahertz wave reflected on the optical member (not illustrated) disposed on the optical path of the terahertz wave between the transmitting unit 101 and the receiving unit 102, the subject 130, and the like may be reduced.

Therefore, destabilization of output of the generating element 111 that generates the terahertz wave may be reduced. Further, a fluctuation in intensity of the detection signal of the receiving unit 102 due to an interference of the terahertz wave reflected on an optical member (not illustrated) disposed on an optical path of the terahertz wave between the transmitting unit 101 and the receiving unit 102, the subject 130, and the like may be reduced. Therefore, a small sized, high resolution sensor capable of obtaining a terahertz wave stably is implementable.

Example 3

Figure 5:
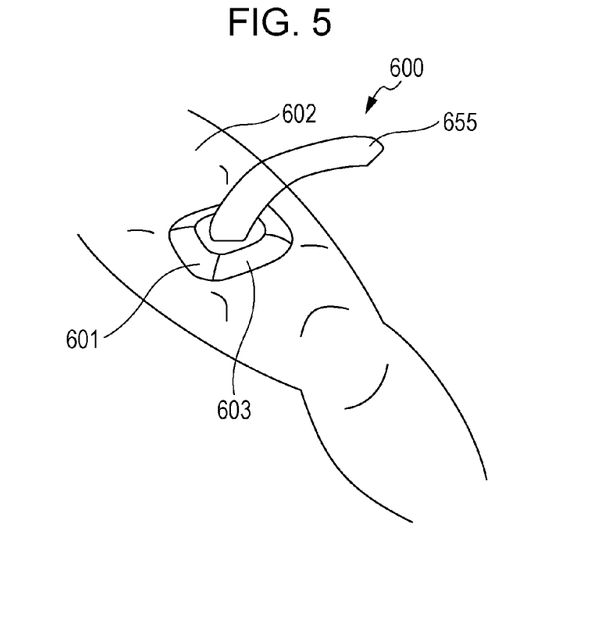
FIG. 5 schematically illustrates a configuration of an information acquisition apparatus of Example 3.

In Example 3, an information acquisition apparatus 600 (hereafter, referred to as an "apparatus 600") for acquiring information on a subject 602 is described. FIG. 5 schematically illustrates a configuration of the apparatus 600. In the example of FIG. 5, a persons' thigh is the subject 602, and an image of the subject 602 is acquired as information on the subject 602.

The apparatus 600 is provided with a probe 601, and an information acquisition unit 655 (hereafter, referred to as an "acquisition unit 655"). The probe 601 incorporates a sensor 100. A transmitting unit 101 and a receiving unit 102 of the sensor 100 are disposed to face the subject 602. A terahertz wave transmitted by the transmitting unit 101 is emitted from the probe 601 and is applied to the subject 602. The terahertz wave reflected on the subject 602 enters the probe 601 again, and is detected by the receiving unit 102 of the sensor 100 disposed inside the probe 601.

A detection result of the receiving unit 102 is transmitted to the acquisition unit 655. The acquisition unit 655 processes the detection result of the receiving unit 102 and acquires information on the subject 602. The acquisition unit 655 may be a computer equipped with a CPU, memory, a storage device, and so on and is connected with the probe 601 by for example a cable. The probe 601 and the acquisition unit 655 may be connected in any manner, for example, wirelessly, for transmission and reception of data.

The subject 602 is not limited to a thigh but may be a touchable living body tissue. For example, the subject 602 is a living body tissue exposed by a surgical operation. Since a terahertz wave discriminates between a cancer tissue and a normal tissue, the probe 601 may be used to examine the existence of a cancer in a patient.

In the probe 601 used in contact with the subject, a window 603 may be desirably provided to be brought into contact with the subject during inspection, and the terahertz wave may be applied via the window 603. A polarization converting unit 104 may be used as the window 603. When the window 603 and the subject 602 are brought into contact with each other, a surface of the subject 602 becomes flat, and the terahertz wave reflected on the subject 602 can be detected accurately by the receiving unit 102. The window 603 can prevent the probe 601 from becoming dirty due to contact between the probe 601 and the subject 602.

The window 603 is formed by a material that transmits the terahertz wave well, i.e., that is transparent to the terahertz wave.

If the probe 601 includes a member that is in contact with the window 603, a dielectric constant of the window 603 is desirably as close as possible to that of the member in contact with the window 603. Therefore, impedance mismatching between the window 603 and the member in contact with the window 603 is prevented. The dielectric constant of the window 603 is desirably different from that of the subject 602. Therefore, reflectance on an interface between the subject 602 and the window 603 may be relatively increased, and an S/N ratio is increased by decreasing the reduction of intensity in the terahertz wave entering the receiving unit 102.

Resolution of the apparatus 600 in the horizontal direction depends on a distance between adjoining receiving units 102 integrated on the substrate 103 of the sensor 100. The apparatus 600 may be used in contact or not in contact with the subject 602. For example, if the apparatus 600 is used to inspect the subject 602 which is a living body tissue exposed by a surgical operation, since the subject 602 is in a sensitive condition, the apparatus 600 is desirably used not in contact with the subject 602. However, accuracy of information on the subject 602 to be acquired, resolution of the acquired image of the subject 602, and the like may become higher when the apparatus 600 is used for inspection in contact with a surface of the subject 602 than when not in contact with the surface of the subject 602.

Also in the apparatus 600, entering, into the transmitting unit 101, of the terahertz wave reflected on an optical member (not illustrated) disposed on an optical path of the terahertz wave between the transmitting unit 101 and the receiving unit 102, the subject, and the like may be reduced, whereby an influence of the terahertz wave may be reduced. Therefore, destabilization of output of the generating element 111 that generates the terahertz wave may be reduced. Further, a fluctuation in intensity of the detection signal of the receiving unit 102 due to an interference of the terahertz wave reflected on an optical member (not illustrated) disposed on an optical path of the terahertz wave between the transmitting unit 101 and the receiving unit 102, the subject 130, and the like may be reduced. Therefore, a small sized, high resolution probe capable of obtaining a terahertz wave stably is implementable.

Example 4

Figure 6:
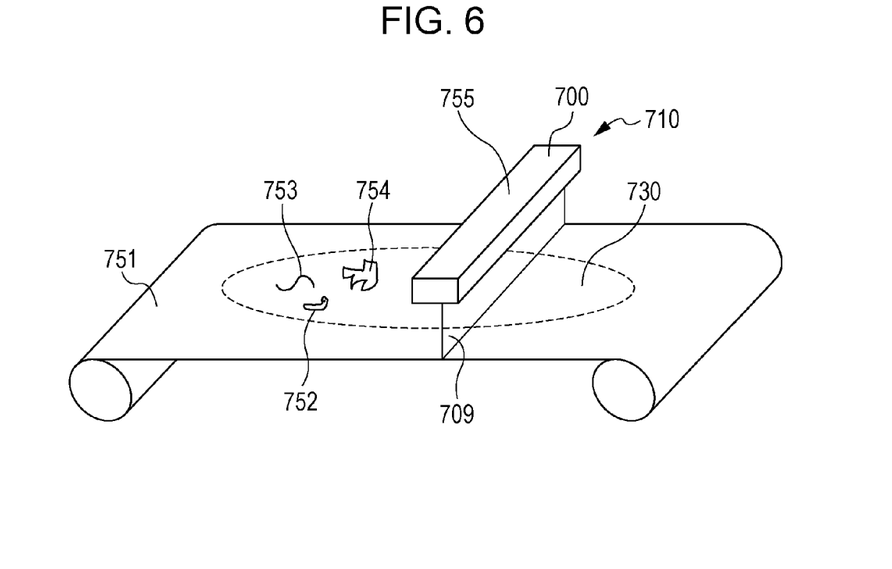
FIG. 6 schematically illustrates a configuration of an information acquisition apparatus according to Example 4.

An information acquisition apparatus 710 (hereafter, referred to as an "apparatus 710") in which the sensor 100 is used is described. FIG. 6 schematically illustrates a configuration of the apparatus 710. The apparatus 710 is provided with a linear sensor 700 that applies a terahertz wave 709 linearly to a subject 730 and detects the terahertz wave 709 reflected on the subject 730, and an information acquisition unit 755 (hereafter, referred to as an "acquisition unit 755").

The linear sensor 700 has a plurality of sensors 100, and a plurality of sensors 100 are arranged in a manner such that a transmitting unit 101 and a receiving unit 102 of each of the sensors 100 face the subject 730. The linear sensor 700 applies the terahertz wave 709 to the subject 730 disposed on a conveyor belt 751, and receives the terahertz wave 709 reflected on the subject 730. The terahertz wave 709 reflected on the subject 730 is converted into second polarization in the polarization direction that crosses the polarization direction of the terahertz wave 709 (i.e., a first polarization direction) by a quarter wavelength plate 104 provided in the linear sensor 700.

The acquisition unit 755 acquires information, such as existence of a foreign substance in the subject 730, and conditions and characteristics of the subject 730, using a detection result of the receiving unit 102 of the linear sensor 700. The acquisition unit 755 is a computer provided with a CPU, memory, a storage device, and so on. Examples of the foreign substance of the subject 730 herein may be a tiny creature 752, hair 753, aluminum foil 754, and the like but these are not restrictive. The acquisition unit 755 determines whether a foreign substance exists in the subject 730, acquires conditions and characteristics of the subject 730, and the like, and feeds back the result to a system that manages the process.

The apparatus 710 may be used as an inspection system that acquires information on, and examines foreign substances in the subject 730, such as molded articles, like powder, pellet, and film, in a production process of food, medical supplies, and chemical materials, or final products packed with paper, plastic material, and the like.

Here, in Example 4, a noncontact linear sensor 700 is described, but a contact linear sensor may also be used. Alternatively, the linear sensors 700 may be disposed on both sides of the conveyor belt 751 to receive and detect the terahertz wave 709 reflected on the subject 730.

According to the apparatus 710 of Example 4, entering, into the transmitting unit 101, of the terahertz wave reflected on an optical member (not illustrated), the subject 130, and the like disposed on an optical path of the terahertz wave between the transmitting unit 101 and the receiving unit 102 may be reduced. That is, an influence of terahertz wave reflected on the optical member, the subject, and the like disposed on an optical path between the transmitting unit of the sensor and the receiving unit of the sensor may be reduced.

Therefore, destabilization of output of the generating element 111 that generates the terahertz wave may be reduced. Further, a fluctuation in intensity may be reduced in the detection signal of the receiving unit 102 due to an interference of the terahertz wave reflected on an optical member (not illustrated), the subject 130, and the like disposed on an optical path of the terahertz wave between the transmitting unit 101 and the receiving unit 102. Therefore, a small sized, high resolution, high speed and high sensitivity inspection system is implementable.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The embodiment described above and each Example may be combined without departing from the scope of the present invention. For example, although the modification of the sensor 100 is described in Example 1, each of the modifications may be combined. Further, although the apparatus 600 provided with the sensor 100 is described in Example 3 and the linear sensor 700 provided with the sensor 100 in Example 4, the sensors described in Examples 1 and 2 may be combined; the sensor configuration may be selected depending on application, usage condition, and so on.

This application claims the benefit of Japanese Patent Application No. 2014-242519, filed Nov. 28, 2014 which is hereby incorporated by reference herein in its entirety.

What is claimed is:

1. A sensor to transmit and detect an electromagnetic wave, the sensor comprising:
a substrate;
a transmitting unit and a receiving unit integrated on the substrate; and
a polarization converting unit,
wherein the transmitting unit includes:
a generating element configured to generate a first electromagnetic wave, and
a first antenna electrically connected with the generating element and configured to emit the first electromagnetic wave, wherein the first electromagnetic wave emitted by the first antenna has a first polarization direction,
wherein the polarization converting unit is configured to convert the first electromagnetic wave into a third electromagnetic wave having a third polarization direction for reflection on a subject, and convert the reflected third electromagnetic wave into a second electromagnetic wave having a second polarization direction,
wherein the receiving unit includes:
a second antenna configured to receive the second electromagnetic wave having a second polarization direction, and
a detecting device electrically connected with the second antenna and configured to detect the second electromagnetic wave received by the second antenna,
wherein, to reduce a change of a characteristic of the generating element by reflected electromagnetic waves entering into the transmitting unit, the polarization converting unit converts a polarization state of the first electromagnetic wave such that combining a reflected electromagnetic wave, having a polarization state that differs from the polarization state of the reflected first electromagnetic wave, with the first antenna is more difficult than combining the reflected first electromagnetic wave with the first antenna.

2. The sensor according to claim 1, wherein the second antenna is selectively combined with the second electromagnetic wave having the second polarization direction.

3. The sensor according to claim 1, wherein the polarization converting unit includes a first converting unit configured to convert the first electromagnetic wave into the third electromagnetic wave having the third polarization direction; and include a second converting unit configured to convert the reflected third electromagnetic wave into the second electromagnetic wave having the second polarization direction.

4. The sensor according to claim 3,
wherein the first converting unit is disposed on a propagation path between transmission of an electromagnetic wave from the transmitting unit and arrival at the subject, and
wherein the second converting unit is disposed on a propagation path after the third electromagnetic wave reflects on the subject until an electromagnetic wave enters the receiving unit.

5. The sensor according to claim 1, wherein the polarization converting unit is disposed on a propagation path between transmission of an electromagnetic wave from the transmitting unit and arrival at the subject, or on a propagation path between reflection of an electromagnetic wave on the subject and the reflected electromagnetic wave entering the receiving unit.

6. The sensor according to claim 1, wherein each first polarization direction and the second polarization direction is linear polarization, and the first polarization direction and the second polarization direction cross each other.

7. The sensor according to claim 6, wherein the first polarization direction and the second polarization direction perpendicularly cross each other.

8. The sensor according to claim 1, wherein the polarization converting unit includes a quarter wavelength plate that is disposed in a manner such that a crystal axis thereof rotates with respect to an optical axis of the first electromagnetic wave having the first polarization direction and an optical axis of the second electromagnetic wave having the second polarization direction.

9. The sensor according to claim 8, wherein the quarter wavelength plate is disposed with an angle between a fast axis/a slow axis and the first polarization direction is 45°.

10. The sensor according to claim 1, wherein the receiving unit is a plurality of receiving units,
wherein a distance between adjoining receiving units of the plurality of receiving units or a distance between adjoining transmitting unit and receiving unit is equal to or shorter than twice a wavelength of each electromagnetic wave.

11. The sensor according to claim 1, wherein the polarization converting unit is integrated on the transmitting unit and the receiving unit.

12. The sensor according to claim 1,
wherein the first antenna includes a first conductor, a second conductor, and a first dielectric material is disposed between the first conductor and the second conductor,
wherein the second antenna includes a third conductor, a fourth conductor, and a second dielectric material is disposed between the third conductor and the fourth conductor,
wherein the generating element is disposed between the first conductor and the second conductor, and at a position shifted from a centroid of the first conductor,
wherein the detecting device is disposed between the third conductor and the fourth conductor, and at a position shifted from a centroid of the third conductor, and
wherein a line connecting the generating element and the centroid of the first conductor and a line connecting the detecting device and the centroid of the third conductor cross each other.

13. The sensor according to claim 1, further comprising a conductor,
wherein each of the first antenna and the second antenna is a slot antenna including an opening provided in the conductor, and
wherein a longitudinal direction of the opening of the first antenna and a longitudinal direction of the opening of the second antenna cross each other.

14. The sensor according to claim 1,
wherein the generating element includes a negative resistance device,
wherein the detecting device includes a rectifier,
wherein the rectifier is a Schottky barrier diode,
wherein each of the first antenna and the second antenna is a resonator, and
wherein the transmitting unit and the receiving unit are disposed side by side on a surface of the substrate.

15. An information acquisition apparatus comprising:
the sensor according to claim 1; and
an information acquisition unit configured to acquire information of the subject using a detection result of the detecting device.

16. The sensor according to claim 1, wherein an electromagnetic wave generated by the generating element includes a terahertz wave that has a frequency that is equal to or higher than 30 GHz and equal to or lower than 30 THz.

17. The sensor according to claim 1, wherein a distance between the transmitting unit and the receiving unit adjoining each other is equal to or shorter than twice a wavelength of an electromagnetic wave generated by the generating element.

18. The sensor according to claim 1, wherein a polarization state of the first polarization direction and a polarization state of the second polarization direction differ from each other.

19. The sensor according to claim 18, wherein, to reduce a chance of change in a characteristic of the generating element in a case where the first antenna is irradiated with reflected electromagnetic waves, the conversion of electromagnetic waves by the polarization converting unit is such that a probability that the first antenna is combined with a reflected second electromagnetic wave is reduced.

20. The sensor according to claim 19, wherein, to reduce a chance of change in a characteristic of the generating element in a case where the first antenna is irradiated with reflected electromagnetic waves, the conversion of electromagnetic waves by the polarization converting unit is such that a probability that the first antenna is combined with a reflected second electromagnetic wave is prevented.

* * * * *